United States Patent
Ida

(10) Patent No.: US 9,939,369 B2
(45) Date of Patent: Apr. 10, 2018

(54) LUBRICANT DETERIORATION SENSOR

(71) Applicant: NABTESCO CORPORATION, Tokyo (JP)

(72) Inventor: Yasuhito Ida, Tokyo (JP)

(73) Assignee: NABTESCO CORPORATION, Tokyo (JP)

(*) Notice: Subject to any disclaimer, the term of this patent is extended or adjusted under 35 U.S.C. 154(b) by 44 days.

(21) Appl. No.: 15/030,753

(22) PCT Filed: Oct. 24, 2014

(86) PCT No.: PCT/JP2014/078403
§ 371 (c)(1),
(2) Date: Apr. 20, 2016

(87) PCT Pub. No.: WO2015/060444
PCT Pub. Date: Apr. 30, 2015

(65) Prior Publication Data
US 2016/0252448 A1     Sep. 1, 2016

(30) Foreign Application Priority Data
Oct. 25, 2013 (JP) .................................. 2013-222382

(51) Int. Cl.
| | | |
|---|---|---|
| *G01N 33/28* | (2006.01) | |
| *G01N 21/25* | (2006.01) | |
| *G01N 21/85* | (2006.01) | |

(52) U.S. Cl.
CPC ........... *G01N 21/25* (2013.01); *G01N 21/255* (2013.01); *G01N 21/8507* (2013.01); *G01N 33/2888* (2013.01); *G01N 2201/127* (2013.01)

(58) Field of Classification Search
CPC .... G01N 21/25; G01N 21/31; G01N 21/8507; G01N 33/2888; G01N 2201/127
(Continued)

(56) References Cited

U.S. PATENT DOCUMENTS

| | | | |
|---|---|---|---|
| 6,184,529 B1 * | 2/2001 | Contini | G01J 1/04 250/252.1 |
| 2009/0216464 A1 | 8/2009 | Kong et al. | |

(Continued)

FOREIGN PATENT DOCUMENTS

| | | |
|---|---|---|
| EP | 2829864 A1 | 1/2015 |
| JP | S61-264238 A | 11/1986 |

(Continued)

OTHER PUBLICATIONS

International Preliminary Report on Patentability and the Written Opinion of the International Searching Authority as issued in International Patent Application No. PCT/JP2014/078403, dated Apr. 26, 2016.

(Continued)

*Primary Examiner* — Hina F Ayub
(74) *Attorney, Agent, or Firm* — Pillsbury Winthrop Shaw Pittman, LLP

(57) ABSTRACT

A lubricant deterioration sensor that can determine a deterioration degree of lubricant without using an external device is provided. The lubricant deterioration sensor includes an oil entering gap in which lubricant to be detected enters, a LED (21) that emits detection light to the oil entering gap, a color sensor (22) that obtains a detection value representing color information of the detection light traveled through the lubricant, a calibration unit that calibrates a measurement range of the detection value in accordance with the lubricant, a determination unit that determines a deterioration degree of the lubricant based on the detection value, and a housing in which the oil entering gap, the LED (21), the color element (22), the calibration unit, and the determination unit are disposed.

8 Claims, 5 Drawing Sheets

(58) Field of Classification Search
USPC .......................................................... 356/70
See application file for complete search history.

(56) References Cited

U.S. PATENT DOCUMENTS

2010/0157304 A1* 6/2010 Takahashi ............... F16C 19/52
356/442
2012/0086942 A1   4/2012 Honda et al.
2015/0288983 A1* 10/2015 Koo ..................... H04N 19/597
375/240.12

FOREIGN PATENT DOCUMENTS

| JP | S62-88942 A | 4/1987 |
| JP | S63-184040 A | 7/1988 |
| JP | H02-187650 A | 7/1990 |
| JP | H05-107184 A | 4/1993 |
| JP | 2008-032548 A | 2/2008 |
| JP | 2012-117951 A | 6/2012 |
| JP | 2013-088371 A | 5/2013 |
| JP | 2013-156170 A | 8/2013 |
| WO | WO 2010/150526 A1 | 12/2010 |
| WO | 2013141260 A1 | 9/2013 |

OTHER PUBLICATIONS

International Search Report as issued in International Patent Application No. PCT/JP2014/078403, dated Jan. 20, 2015.
Extended European Search Report EP Application No. 14856701.9 dated May 31, 2017.

* cited by examiner

LUBRICANT DETERIORATION SENSOR

CROSS-REFERENCE TO RELATED APPLICATIONS

This application is the U.S. National Stage of PCT/JP2014/078403, filed Oct. 24, 2014, which in turn claims priority to Japanese Patent Application No. JP 2013-222382, filed Oct. 25, 2013. The contents of these applications are incorporated herein by reference in their entireties.

TECHNICAL FIELD

The present invention relates to a lubricant deterioration sensor that detects deterioration of lubricant used in machines.

BACKGROUND

Conventional lubricant deterioration sensors detect a red-green-blue (RGB) absorbance in visible light that travels through lubricant and then detect a deterioration degree of the lubricant based on the detected RGB absorbance (see, for example, Patent Literature 1).

The lubricant deterioration sensor disclosed in Patent Literature 1 includes a space where lubricant flows in, an LED that emits a visible light beam toward the space, and an RGB sensor that receives a light beam that is emitted from the LED and traveled through the space. In the lubricant deterioration sensor, the LED emits a light beam and the RGB sensor receives the light beam. A result of detection performed by the RGB sensor is output to an external device. The conventional lubricant deterioration sensor does not perform adjustment of its detection accuracy and determination

RELEVANT REFERENCES

List of Relevant Patent Literature

Patent Literature 1: Japanese Patent Application Publication No. 2012-117951

SUMMARY

As described above, in the case of the lubricant deterioration sensor disclosed in Patent Literature 1, a device that is externally provided performs the determination of a deterioration degree of the lubricant. In other words, an external device is required to determine a deterioration level of the lubricant. It is desirable to develop a lubricant deterioration sensor that can determine a deterioration degree of lubricant without using an external device. It is also desirable to develop a lubricant deterioration sensor that can adjust its measurement range and the like without using an external device.

In view of the above, one object of the invention is to provide a lubricant deterioration sensor that can determine a deterioration degree of lubricant without using an external device.

Means and its effects for achieving the object will be now described. According to one aspect of the invention, a lubricant deterioration sensor includes an examination section in which lubricant to be detected enters, a light emitting element that emits detection light to the examination section, a light receiving element that obtains a detection value that represents color information of the detection light traveled through the lubricant, a calibration unit that calibrates a measurement range of the detection value in accordance with the lubricant to be detected, a determination unit that determines a deterioration degree of the lubricant based on the detection value, and a housing in which the examination section, the light emitting element, the light receiving element, the calibration unit, and the determination unit are disposed.

In this way, the detection light emitted from the light emitting element penetrates lubricant disposed in the examination section and the light receiving element detects color information of the detection light that traveled through the lubricant. More specifically, the light receiving element obtains a detection value that represents the color information. The calibration unit then calibrates a measurement range of the detection value detected by the light receiving element based on the lubricant to be detected. In this manner, it is possible to enhance the detection accuracy. The determination unit determines a deterioration degree of the lubricant based on the calibrated detection value. Therefore, it is possible to determine a deterioration degree of lubricant with the lubricant deterioration sensor alone without using an external device and to adjust the measurement range of the detection value without using an external device.

In the lubricant deterioration sensor, the light receiving element may be a first light receiving element, and it is preferable that the lubricant deterioration sensor include a second light receiving element that detects detection light emitted from the light emitting element and obtains a detection result, and the calibration unit calibrate an intensity of light emitted from the light emitting element in accordance with the detection result.

In the above-described configuration, the second light receiving element that directly detects the detection light emitted from the light emitting element is provided. The calibration unit calibrates the intensity of the light in accordance with the detection result from the second light receiving element. When the light emitting element is degraded over time or the intensity of the light is decreased due to temperature change, there may be error caused in the deterioration determination due to change in the detection light caused by the degradation of the light emitting element and the temperature change. However the detection light emitted from the light emitting element can be directly detected so as to check the degradation and temperature change of the light emitting element. By calibrating the intensity of light emitted from the light emitting element, the determination of a deterioration degree of lubricant will not be affected.

In the lubricant deterioration sensor, the light receiving element may be a first light receiving element, and it is preferable that the lubricant deterioration sensor further includes a second light receiving element that detects detection light emitted from the light emitting element and obtains a detection result, and the calibration unit calibrate the detection result in accordance with the detection result.

In the above-described configuration, the second light receiving element that directly detects the detection light emitted from the light emitting element is provided. The calibration unit calibrates the detection value in accordance with the detection result from the second light receiving element. When the light emitting element is degraded over time or the intensity of the light is decreased due to temperature change, there may be error caused in the deterioration determination due to change in the detection light caused by the degradation of the light emitting element and the temperature change. However the detection light emitted from the light emitting element can be directly detected so as to check the degradation and temperature change of the light emitting element. By calibrating the detection value, the determination of a deterioration degree of lubricant will not be affected.

In the lubricant deterioration sensor, it is preferable that the determination unit obtain a plurality of the detection values and a mode of the detection values is used for determination. Lubricant sometimes contains air bubbles. An attenuation of the detection light traveled through a portion of the lubricant that contains air bubbles is smaller than that of the detection light traveled through a portion of the lubricant that does not contain air bubbles. Therefore a detection value corresponding to the portion of the lubricant containing air bubbles may be larger than an inherent detection value that should be obtained for the lubricant to be detected. In the above-described configuration, the determination unit obtains a plurality of detection values and the mode of the detection values is used for the deterioration determination. In this manner, detection values that are larger than the inherent detection value are excluded as noise and detection values that are considered to be correct are used for the determination of lubricant deterioration. Therefore it is possible to enhance the detection accuracy.

In the lubricant deterioration sensor, it is preferable that the determination unit obtain a plurality of the detection values and a minimum value among the detection values is used for determination. Lubricant sometimes contains air bubbles. As for a colored lubricant, an attenuation of the detection light traveled through a portion of the lubricant that contains air bubbles is smaller than that of the detection light traveled through a portion of the lubricant that does not contain air bubbles. Therefore a detection value corresponding to the portion of the lubricant containing air bubbles may be larger than an inherent detection value that should be obtained for the lubricant to be detected. In the above-described configuration, the determination unit obtains a plurality of detection values and the minimum value among the detection values is used for the determination. In this manner, detection values that are larger than the inherent detection value are excluded as noise and detection values that are considered to be correct are used for the determination of lubricant deterioration. Therefore it is possible to enhance the detection accuracy.

In the lubricant deterioration sensor, it is preferable that the determination unit determine a deterioration degree of the lubricant based on a calculated value using at least one of a brightness or a maximum color-component difference calculated from the detection value.

In the above-described configuration, the determination unit uses at least one of a brightness or a maximum color-component difference (a maximum color difference) calculated from the detection value to determine a deterioration degree of lubricant. When lubricant is contaminated with impurities generated from a machine, a brightness of the lubricant prominently changes so that a deterioration degree of the lubricant can be easily determined. Moreover, in a case of lubricant in which a color of a base oil is easily changed by oxidation, degradation or the like, the maximum color difference significantly changes so that a deterioration degree of the lubricant can be easily determined. Furthermore, by combining the brightness and the maximum color difference, it is possible to determine a degradation degree of lubricant even when at least one of the contamination or the color change of the base oil occurs in the lubricant.

In the lubricant deterioration sensor, it is preferable that the calibration unit obtain an initial value by calibrating the calculated value, and the determination unit perform determination of a deterioration degree of the lubricant when there is a prescribed amount of change in the calculated value from the initial value.

In the above-described configuration, when there is a prescribed amount of change in the calculated value from the initial value, the determination unit performs determination of a deterioration degree of the lubricant. Because there is a certain amount of change from the initial value, it is possible to easily determine a deterioration degree of the lubricant.

In the lubricant deterioration sensor, it is preferable that the determination unit determine damage of a machine that uses the lubricant based on the detection value. When a machine in which lubricant is used is broken, impurities are generated. According to the above configuration, the determination unit utilizes the detection value to determine failure of the machine in which the lubricant is used. In this way, it is possible to easily determine the failure of the machine through the detection value that has changed due to the impurities.

According to another aspect of the invention, a lubricant deterioration sensor includes a determination unit that determines a deterioration degree of lubricant based on an intensity of light traveled through the lubricant to be detected. In this configuration, it is possible to determine a deterioration degree of lubricant by the lubricant deterioration sensor without using an external device.

In the lubricant deterioration sensor, it is desirable to provide a calibration unit that calibrates a measurement range of the intensity of the light in accordance with the lubricant to be detected. In this manner, it is possible to adjust the measurement range of the intensity of the light without using an external device.

Advantages

According to the above-described aspects of the invention, it is possible to determine a deterioration degree of lubricant without using an external device.

DESCRIPTION OF THE PREFERRED EMBODIMENTS

Figure 2:
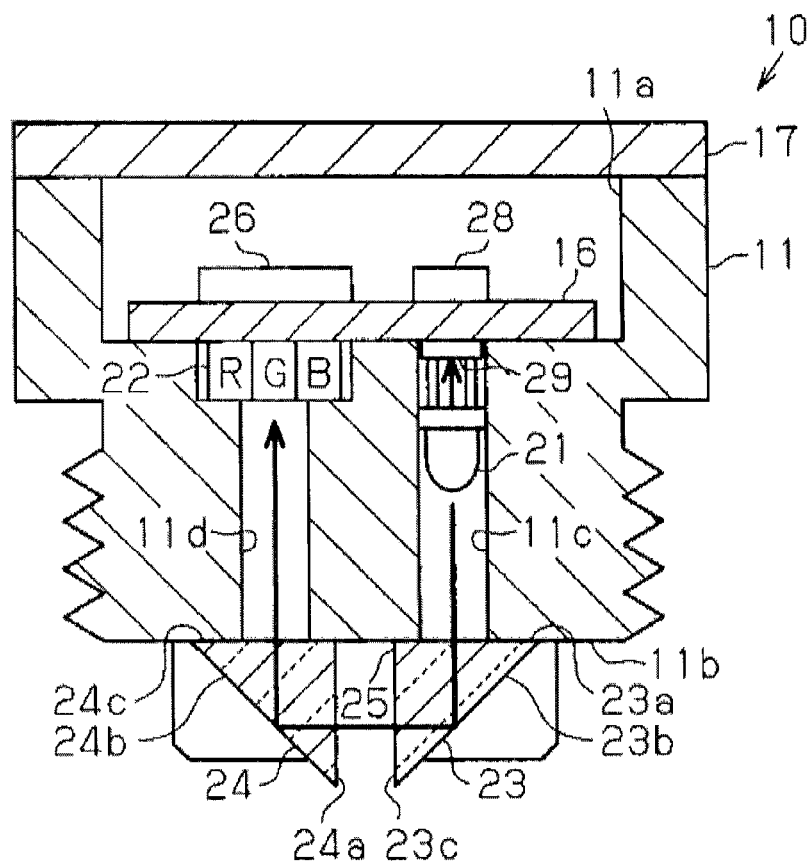
FIG. 2 is a sectional view of the lubricant deterioration sensor of FIG. 1 illustrating its schematic structure.
Figure 3:
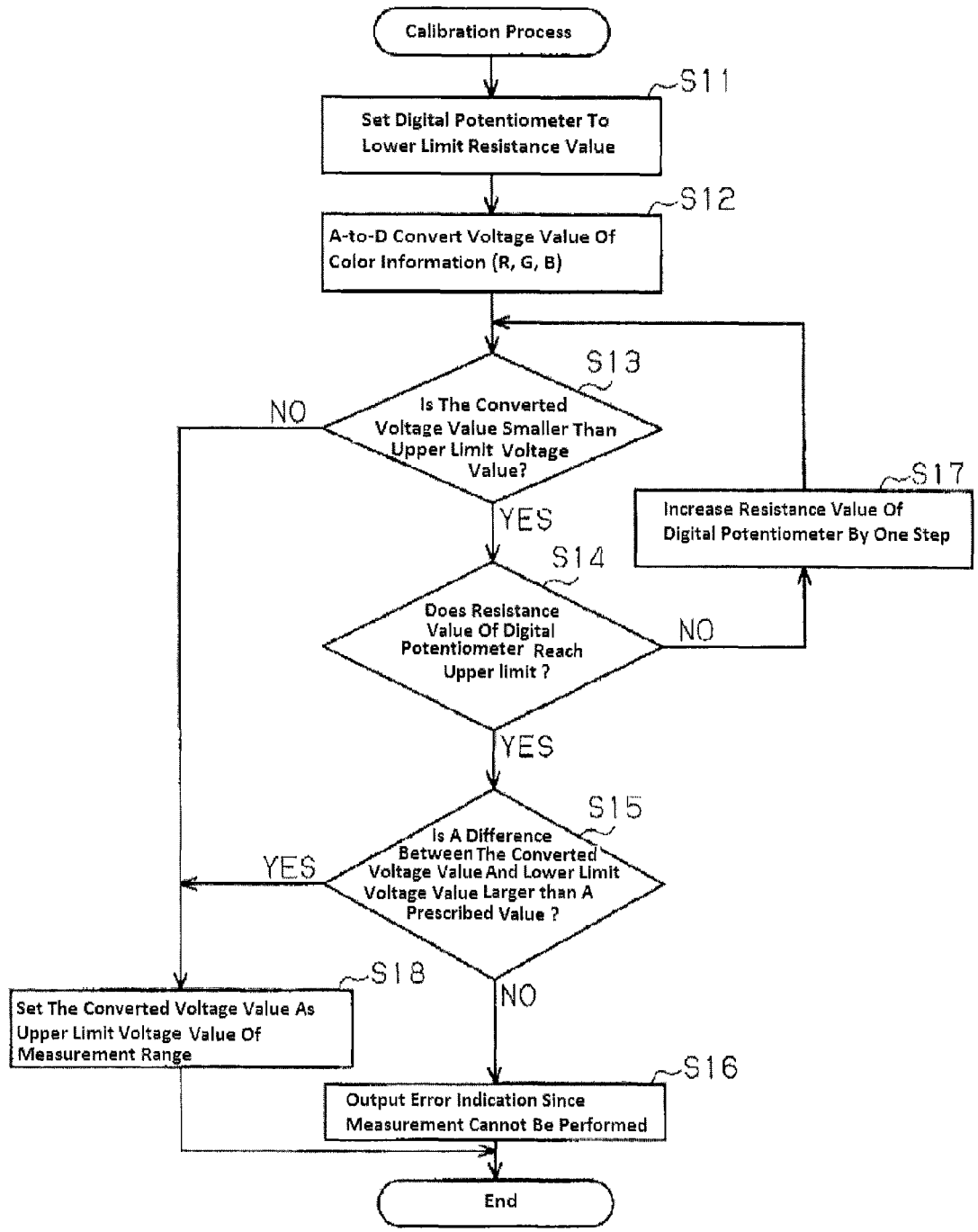
FIG. 3 is a flow chart of a calibration process performed by the lubricant deterioration sensor of FIG. 1.

One embodiment of a lubricant deterioration sensor will be now described with reference to FIGS. 1-3. A lubricant deterioration sensor may be provided to machines that use lubricant, and the lubricant deterioration sensor determines a deterioration degree of the lubricant and a machine failure. When a movable part that requires lubricant in a machine is broken, the lubricant is often contaminated with impurities generated by abrasion and the like of the movable part. In this way, it is possible to determine the machine failure from the state of the lubricant. Note that the embodiment encompasses a hydraulic fluid as the lubricant.

Figure 1:
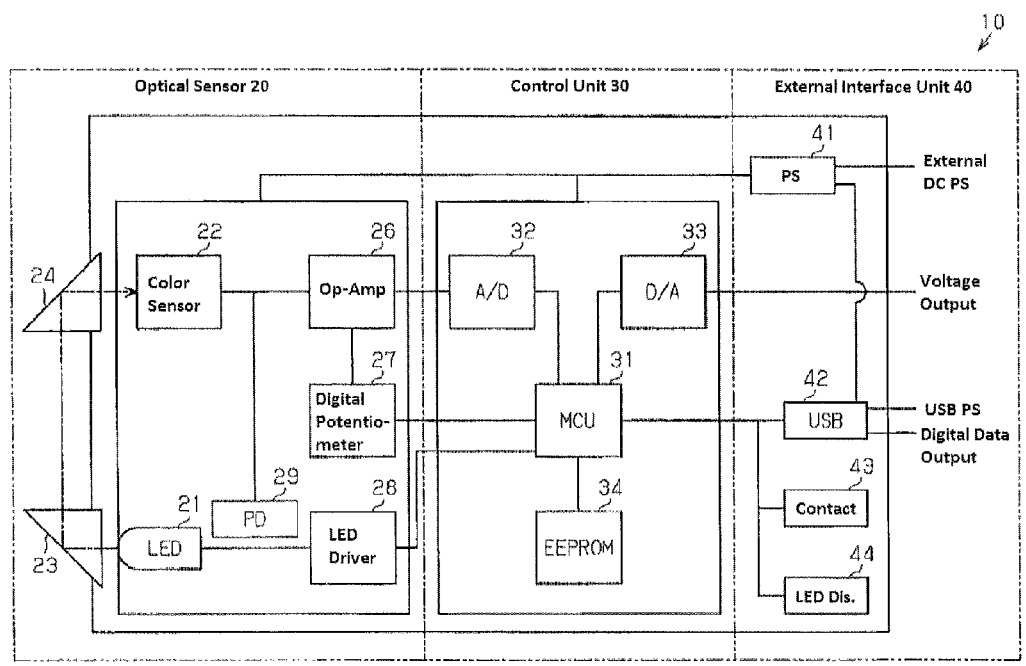
FIG. 1 is a block diagram illustrating a schematic structure of a lubricant deterioration sensor according to one embodiment.

Referring to FIG. 1, a lubricant deterioration sensor 10 may generally include an optical sensor unit 20 in which detection light is emitted and detected, a control unit 30 in which various controls and determination of deterioration of lubricant are performed, and an external interface unit 40 that mediates supplying information and electric power to/from external devices.

The optical sensor unit 20 may include a light emitting diode (LED) 21 that is a light emitting element, a first prism 23 and a second prism 24 that reflect the detection light, a color sensor 22 that is a light receiving element (a first light receiving element) that detects color information of the detection light, and a photodiode (PD) 29 that is a second light receiving element detecting direct light from the LED 21. The optical sensor unit 20 may further include an operational amplifier 26 that amplifies voltage values output from the color sensor 22 and the photodiode 29, a digital potentiometer 27 that calibrates a measurement range of a voltage output by the operational amplifier 26, and a LED driver 28 that drives the LED 21.

The control unit 30 may include a micro control unit (MCU) 31 that performs various controls and determines a degree of deterioration of lubricant, and an analog-to-digital converter circuit (A/D converter circuit) 32 that coverts an analog voltage value output by the operational amplifier 26 to a digital value. The control unit 30 may further include a digital-to-analog converter circuit (D/A converter circuit) 33 that converts the digital value output by the MCU 31 to an analog voltage value, and an electrically erasable programmable read only memory (EEPROM) 34 that stores determination threshold values, measurements data and the like. The digital potentiometer 27 and the LED driver 28 may be controlled by the MCU 31. When the MCU 31 outputs a voltage value, the digital value is converted through the D/A converter circuit 33 to the voltage value.

The external interface unit 40 may include a power supply 41 that is powered by an external DC power source, an USB 42 that is powered by an USB power supply and performs output and input of digital data, a contact point 43, and display LEDs 44 that indicate a deterioration state of lubricant. The display LEDs 44 may include, for example, red, yellow, and green LEDs and indicate a deterioration state of lubricant, an error state of the sensor and the like by selectively activating the LEDs.

The lubricant deterioration sensor 10 may perform a calibration process onto an initial detection value in order to maintain an accuracy of detection values. More specifically, the operational amplifier 26 and the digital potentiometer 27 may be non-inverting amplifier circuits. An amplification factor of the operational amplifier 26 is able to be adjusted through a variable resistance of the digital potentiometer 27. Lubricant to be detected may be colored depending on the intended use and the initial value of the detection value may vary depending on a type of the lubricant. When a voltage value output by the operational amplifier 26 is input into the MCU 31 through the A/D converter circuit 32, the MCU 31 may determine whether the amplification factor is appropriate and if more amplification is required, the MCU 31 may instruct the digital potentiometer 27 to increase the amplification factor gradually. The MCU 31 may initially set a resistance value of the digital potentiometer 27 to a lower limit resistance value and then increase the amplification factor by increasing the resistance value while seeing the voltage value input thereto. The MCU 31 may adjust the voltage value to be a predetermined voltage value. As described above, the calibration of the measurement range of the detection value detected by the color sensor 22 may be performed by the MCU 31, the digital potentiometer 27, and the operational amplifier 26. In other words, the MCU 31, the digital potentiometer 27, and the operational amplifier 26 together serve as a calibration unit.

When the photodiode 29 directly detected detection light from the LED 21, the photodiode 29 may output, to the MCU 31, a detection value that is a voltage value converted from the intensity of the detection light through the operational amplifier 26 and the A/D converter circuit 32. When the input voltage value is lower than a predetermined voltage value that is smaller than the initial voltage value, the MCU 31 may determine that the LED 21 is deteriorated. In order to calibrate the deterioration of the LED 21, the MCU 31 may control the LED driver 28 such that the LED 21 emits an amount of light which the LED 21 initially emitted. More specifically, the LED driver 28 may increase the amount of electric current running through the LED 21 by performing a current control utilizing resistance to adjust the amount of light. For example, the resistance of the current control in the LED driver 28 may be replaced by the digital potentiometer 27 and the MCU 31 may control the digital potentiometer 27 to change the amount of current running through the LED 21.

The MCU 31 may read out a voltage value from the digital value converted by the A/D converter circuit 32 to determine whether measurement is possible or not, and an error output is performed. The error output may be performed through outputting an error signal from the USB 42 as a digital signal, and/or activating a set of the display LEDs 44 to show an error indication. The display LEDs 44 may be turned on in the following manners. When lubricant is new or substantially no deterioration (a normal state), only a green LED is activated. When the lubricant is deteriorated to some extent (caution), only a yellow LED is activated. When the lubricant is seriously deteriorated, only a red LED is activated. When the lubricant deterioration sensor 10 is not able to measure the lubricant (an abnormal state), all of the green, yellow and red LEDs are blinked on and off.

Figure 4:
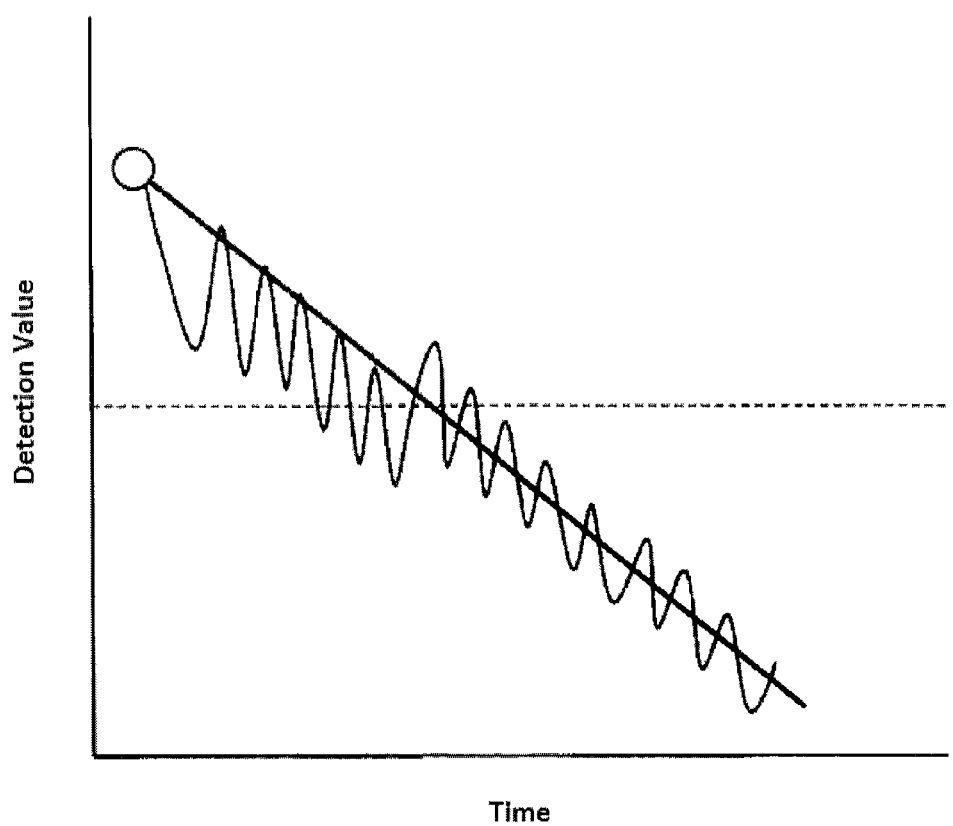
FIG. 4 illustrates change in a detection value of a substantially transparent and colorless lubricant over time detected by the lubricant deterioration sensor of FIG. 1.

Referring to FIG. 4, in the case of a substantially colorless and transparent lubricant, a detection value for a portion of the lubricant that does not contain air bubbles may linearly decrease over time from the point of a brand-new lubricant denoted as an open circle. An attenuation of the detection light traveled through a portion of the lubricant that contains air bubbles is larger than that of the detection light traveled through the portion of the lubricant that does not contain air bubbles. Therefore a detection value corresponding to the portion of the lubricant containing air bubbles may be smaller than an inherent detection value that should be obtained for the lubricant to be detected. Furthermore as indicated by an area below the broken line in FIG. 4, in the case of a deteriorated colored lubricant, an attenuation of the detection light traveled through a portion of the lubricant that contains air bubbles is smaller than an attenuation of the detection light traveled through a portion of the lubricant that does not contain air bubbles. Therefore a detection value corresponding to the portion of the lubricant containing air bubbles may be larger than an inherent detection value that should be obtained for the lubricant to be detected. Consequently, as for the deteriorated and colored lubricant that includes air bubbles, detection values for light traveled through a portion of the lubricant that contains air bubbles and light traveled through a portion of the lubricant that does not contain air bubbles become larger or smaller than an detection value that should be obtained for the inherent lubricant.

Figure 5:
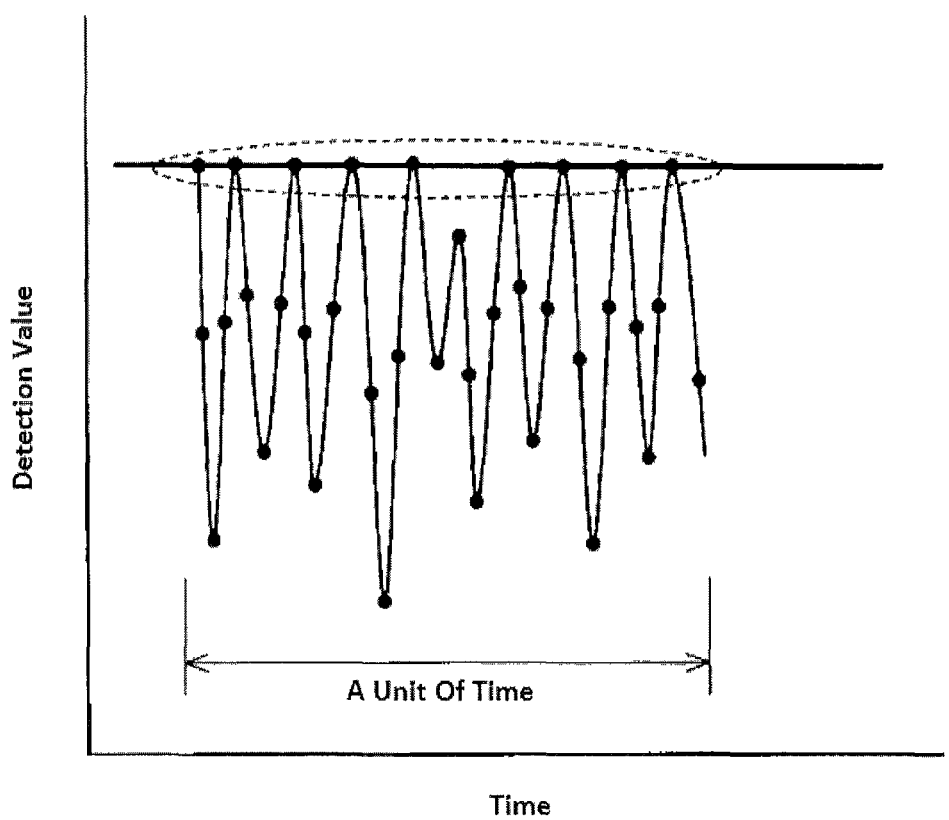
FIG. 5 illustrates a value that appears most often in detection values detected by the lubricant deterioration sensor of FIG. 1.

To address such a difference in the detection values, the MCU 31 may obtain a plurality of detection values in a unit of time as illustrated in FIG. 5. The MCU 31 may adopt a mode of the detection values in the unit of time among the detection values that fluctuate up and down to perform determination. In this manner detection values that largely deviate from the inherent detection value are excluded as noise and detection values that are considered to be correct are used for the determination of lubricant deterioration. Therefore it is possible to enhance the detection accuracy. Referring to FIG. 4, in the case of the colored lubricant, detection values fluctuate up and down with respect to the inherent detection value for the colored lubricant that does not include air bubbles. An attenuation of the detection light traveled through a portion of the lubricant that contains air bubbles is smaller than that of the detection light traveled through a portion of the lubricant that does not contain air bubbles. Therefore an attenuation of the detection light traveled through the portion of the lubricant containing air bubbles may be larger than an inherent detection value that should be obtained for the lubricant to be detected. Therefore, the MCU 31 may obtain a plurality of detection values at a single detection for a colored lubricant and it may adopt the minimum value from among the plurality of detection values for determination. By adopting the minimum of the detection values for the determination, it is possible to improve the detection accuracy.

Referring to FIG. 4, in the case of the substantially colorless and transparent lubricant, detection values tend to be smaller than the inherent detection value for the substantially colorless and transparent lubricant that does not include air bubbles. When the lubricant is not deteriorated and colored, an attenuation of the detection light traveled through a portion of the lubricant that contains air bubbles is larger than that of the detection light traveled through a portion of the lubricant that does not contain air bubbles. Therefore an attenuation of the detection light traveled through the portion of the lubricant containing air bubbles may be smaller than an inherent detection value that should be obtained for the lubricant to be detected. Therefore, the MCU 31 may obtain a plurality of detection values at a single detection for a substantially colorless and transparent lubricant that is not colored by deterioration and it may adopt the maximum value from among the plurality of detection values for determination. By adopting the maximum of the detection values for the determination, it is possible to improve the detection accuracy.

The MCU 31 may estimate, for example, a brightness and a maximum color-component difference and the like from the digital value input thereto. The MCU 31 may then determine whether the estimated brightness and greatest difference of color components and the like reach oil deterioration threshold values over time that are used for determining a degree of deterioration of the lubricant. The MCU 31 may further determine whether the estimated brightness and/or the maximum color difference and the like reaches a machine damage threshold value that is used for determining a machine failure. In this way, the MCU 31 corresponds to a determination unit. When the estimated brightness and/or the maximum color difference and the like reaches the oil deterioration threshold value, only the red LED may be turned on, and when they reach the machine damage threshold value, only the red LED may be blinked on and off.

The oil deterioration threshold value and the machine damage threshold value may be obtained from adjusting the initial values on which a calibration process is performed. In other words, the oil deterioration threshold value and the machine damage threshold value are obtained, irrespective of a type of the lubricant, by changing the initial values by a prescribed amount. When a user has a sample of a deteriorated lubricant, a detection value of the sample may be used as the threshold values. In this way, it is possible to realize an accurate determination. Moreover, in a case of a highly transparent lubricant, a change from the initial value may be very small even when the lubricant is deteriorated. In this case, the threshold values may be determined based on samples and database that a user has. Furthermore, lubricant may be colored by a user and users may color lubricants differently even if the lubricants are the same type. Therefore a provisional threshold value may be specified only based on a type of lubricant and then an appropriate threshold value may be specified for each user. In this way, it is possible to realize an accurate determination.

The brightness may decrease as a operating time of a machine that uses lubricant increases. The brightness ($\Delta E$) is calculated from the formula $\Delta E = \sqrt{(R^2 + G^2 + B^2)}$ wherein R is a R value, G is a G value, and B is a B value. When the MCU 31 determines a deterioration state of a lubricant based on the brightness of the lubricant calculated from the detection value, the MCU 31 may determine the deterioration state of the lubricant based on comparison between the brightness of the lubricant calculated from the detection value and the oil deterioration threshold value. When the brightness is less than or equal to the oil deterioration threshold value, the MCU 31 may determine that the lubricant is deteriorated. When the MCU 31 determines a damaged state of a machine based on the brightness of the lubricant calculated from the detection value, the MCU 31 may determine the deterioration state of the lubricant based on comparison between the brightness of the lubricant calculated from the detection value and the oil deterioration threshold value. The machine damage threshold value is smaller than the oil deterioration threshold value. When the brightness is less than or equal to the machine damage threshold value, the MCU 31 may determine that the machine is damaged.

The maximum difference of color components (the maximum color difference) may increase as an operating time of the machine that uses lubricant increases and then decreases once the maximum color difference reaches the extreme value. A difference between color components is an absolute value represented as $|R-G|$, $|G-B|$, and $|R-B|$ respectively. The one having the largest value among these component color differences is the maximum color difference. The minimum color component value generally corresponds to the B value and the maximum color component value generally corresponds to the R value among the R, G, B values, so only the color difference $|R-B|$ may be calculated as the maximum color difference.

When the MCU 31 determines a deterioration state of a lubricant based on the maximum difference of color components of the lubricant calculated from the detection value, the MCU 31 may determine the deterioration state of the lubricant based on comparison between the maximum difference of color components of the lubricant calculated from the detection value and the oil deterioration threshold value. When the maximum difference of color components passes over the extreme value and is smaller than or equal to the oil deterioration threshold value, the MCU 31 may determine that the lubricant is deteriorated. When the MCU 31 determines a damaged state of a machine based the maximum difference of color components calculated from the detection value, the MCU 31 may determine the deterioration state of the lubricant based on comparison between the maximum difference of color components of the lubricant calculated from the detection value and the machine damage threshold value. The machine damage threshold value is smaller than the oil deterioration threshold value. When the maximum difference of color components passes over the extreme value and is smaller than or equal to the machine damage threshold value, the MCU 31 may determine that the machine is damaged.

The EEPROM 34 may store the oil deterioration threshold value and the machine damage threshold value used for determination together with the detection values of the lubricant that are periodically detected as detection data. A structure of the lubricant deterioration sensor 10 will be now described with reference to FIG. 2.

The lubricant deterioration sensor 10 may include a column-shaped housing 11 made of metal or resin. A container section 11a may be provided in an upper area of the housing 11. The container section 11a may be covered with a cover 17. A male screw is formed on the periphery of a lower area of the housing 11. The lubricant deterioration sensor 10 is attached on a machine using the male screw.

The container section 11a may contain a circuit substrate 16. The circuit substrate 16 may be fixed on the housing 11. The LED 21, the color sensor 22, the photodiode 29, the MCU 31, and various electronic components (not shown) may be provided on the circuit substrate 16. The LED 21 may be a commonly-known element that emits white detection light. The color sensor 22 may be an RGB sensor and output R, G, B values as color information corresponding to an intensity of the detection light. The photodiode 29 may be provided between the LED 21 and the circuit substrate 16 and may detect a light beam emitted in a direction opposite to a light beam that is emitted from the LED 21 toward the first prism 23.

The housing 11 may have a first through hole 11c extending in an optical axis direction of the detection light. The first through hole 11c extends from the bottom of the container section 11a to the bottom of the housing 11. The first prism 23 may be provided on the bottom of the housing 11 at an exit of the first through hole 11c. The first prism 23 may be a right-angle prism made of a translucent material such as quartz and glass. The first prism 23 may have an incident surface 25a where the detection light traveled through the first through hole 11c enters, a reflection surface 25b where the detection light entered from the incident surface 25a is reflected, and an exit surface 25c through which the detection light reflected at the reflection surface 25b exits out.

The incident surface 25a and the exit surface 25c may be optical-polished. The reflection surface 25b may be formed of a metal deposited film and a protection film. The metal deposited film is, for example, a thin aluminum film and formed on the outer side of the translucent material. The protection film is, for example, a silicon dioxide thin film or a magnesium fluoride thin film formed on the outer side of the metal deposited film to protect the metal deposited film. An angle of the reflection surface 25b with the incident surface 25a may be set such that a path of the light entering the reflection surface 25b is reflected at 90 degrees from the incident direction.

The second prism 24 may be provided on the bottom 11b of the housing 11. The second prism 24 may be disposed with a gap from the first prism 23. The second prism 24 may have the same structure as the first prism 23 and have an incident surface 26a, a reflection surface 26b, and an exit surface 26c. The gap between the first prism 23 and the second prism 24 may be an oil entering gap 25 where lubricant enters and stays thereon and the gap serves as an examination section.

The housing 11 may have a second through hole 11d extending in parallel with the first through hole 11c. The second through hole 11d may extend from the bottom of the container section 11a to the bottom 11b of the housing 11 and may be disposed between the second prism 24 and the color sensor 22.

The white detection light beam emitted from the LED 21 travels straight through the first through hole 11c and enters into the first prism 23. The light path of the detection light is then bent at 90 degrees by the reflection surface 25b and enters into the oil entering gap 25 from the exit surface 25c. The detection light further penetrates the lubricant in the oil entering gap 25 and then enters the second prism 24. The light path of the detection light entered the second prism 24 is bent at 90 degrees by the reflection surface 26b and then travels straight through the second through hole 11d Finally, the detection light is received by the color sensor 22. In other words, the light path of the detection light emitted from the LED 21 is reversed 180 degrees by the first prism 23 and the second prism 24. The detection light that has traveled through the lubricant becomes light in which a wavelength region corresponding to the hue of the lubricant is absorbed.

The calibration process performed by the lubricant deterioration sensor 10 configured as described above will be now described with reference to FIG. 3. The calibration process is performed on the initial detection value. More specifically, after the lubricant deterioration sensor 10 is attached to a machine that uses lubricant and when the lubricant enters in the oil entering gap 25 that serves as the examination section, the calibration process may be performed.

For instance, suppose that a measurable range of the A/D converter circuit 32 is 0 V to 5 V and a precision of the A/D converter circuit 32 is 10 bit. And suppose that a lower limit voltage value of a measurement range is 0 V and an upper limit voltage value of the measurement range is 3.5 V, and a user wishes to perform measurements with a resolution of 8 bit (256 steps). Here, the measurable range of the A/D converter circuit 32 is 0 V to 5 V and the precision is 10 bit so that the circuit can read a voltage change of 0.0049 V (5 divided by 1024 equals to 0.0049).

When electric power is supplied to the machine and lubricant enters into the examination section, the MCU 31 may initiate the calibration process. The MCU 31 may set the digital potentiometer 27 to the lower limit resistance value (Step S11). More specifically, the MCU 31 sets the potentiometer to the lower limit resistance value in order to perform the calibration from a lowest amplification factor.

The MCU 31 may then obtain a voltage value output by the color sensor 22 and perform A/D conversion of the voltage value (Step S12). More specifically, the color sensor 22 may receive detection light emitted from the LED 21 and the operational amplifier 26 may amplify the R value, G value, and B value that are the color information corresponding to an intensity of the detection light as a voltage value, and the amplified voltage value is output to the A/D converter circuit 32. The MCU 31 may obtain the voltage value that is a digital value converted by the A/D converter circuit 32.

Subsequently the MCU 31 may determine whether the voltage value amplified by the operational amplifier 26 and converted by the A/D converter circuit 32 is smaller than the upper limit voltage value (Step S13). In other words, the MCU 31 determines whether determination can be performed with 8 bit (256 steps) that is the desired voltage change. When the MCU 31 determines that the voltage value amplified by the operational amplifier 26 and converted by the A/D converter circuit 32 is not smaller than the upper limit voltage (No in Step S13), the voltage value amplified by the operational amplifier 26 and converted by the A/D converter circuit 32 is set as the upper limit voltage value of the measurement range (Step S18). More specifically, since the converted voltage value exceeds the upper limit voltage value (3.5 V), the MCU 31 determines that the deterioration determination is able to be performed with the desired 8-bit (256 steps) voltage change. The MCU 31 then set the current voltage value as the upper limit voltage value of the measurement range.

Whereas when the MCU 31 determines that the voltage value amplified by the operational amplifier 26 and converted by the A/D converter circuit 32 is smaller than the upper limit voltage (Yes in Step S13), the MCU 31 further determines whether the resistance value of the digital potentiometer 27 is the upper limit value or not (Step S14). More specifically, since the converted voltage value does not exceed the upper limit voltage value (3.5 V), the MCU 31 determines that the deterioration determination cannot be performed with the desired 8-bit (256 steps) voltage change. The MCU 31 may then determine whether the resistance value of the digital potentiometer 27 is able to be further increased in order to increase the amplification factor from the current amplification factor value. When the MCU 31 determines that the resistance value of the digital potentiometer 27 is not the upper limit value (No in Step S14), the resistance value of the digital potentiometer 27 is increased by one step (Step S17) and the flow proceeds to Step S13. In other words, since the resistance value of the digital potentiometer 27 is not the upper limit value so that the MCU 31 increases the resistance value by one step in order to increase the current amplification factor, and then the converted voltage value is compared to the upper limit voltage value. The amplification factor of the operational amplifier 26 is adjusted by repeating the Steps S13, S14 and S17.

Whereas when the MCU 31 determines that the resistance value of the digital potentiometer 27 is the upper limit value (Yes in Step S14), the MCU 31 may determine whether a difference between the voltage value that is amplified by the operational amplifier 26 and converted by the A/D converter circuit 32 and the lower limit voltage value of the measurement range is larger than a prescribed value (Step S15). More specifically, when the precision is 10 bit, the minimum voltage range that the A/D converter circuit 32 is able to determine with a 256-step resolution is 1.26 V (multiplying 0.0049 by 256 equals to 1.26). In other words, when there is at least 1.26 V of the difference from the lower limit value of the measurement range that is 0 V in the example, the deterioration determination can be performed even though there is no margin for errors. For this reason, the MCU 31 may compare the difference between the converted voltage value and the lower limit voltage value of the measurement range to the prescribed value (1.26 V). When the MCU 31 determines that the difference between the voltage value amplified by the operational amplifier 26 and converted by the A/D converter circuit 32 and the lower limit voltage value of the measurement range is equal to or larger than the prescribed value (Yes in Step S15), the voltage value amplified by the operational amplifier 26 and converted by the A/D converter circuit 32 is set as the upper limit voltage value of the measurement range (Step S18), and the calibration process is completed. More specifically, since the difference between the converted voltage value and the lower limit voltage value of the measurement range is equal to or larger than the prescribed value (1.26 V), the MCU 31 can perform the measurement and sets the voltage value as the upper limit voltage value of the measurement range.

Whereas when the MCU 31 determines that the difference between the voltage value amplified by the operational amplifier 26 and converted by the A/D converter circuit 32 and the lower limit voltage value of the measurement range is smaller than the prescribed value (No in Step S15), the MCU 31 may output an error indication since the measurement is not able to be performed (Step S16) and the calibration process is completed. More specifically, since the difference between the converted voltage value and the lower limit voltage value of the measurement range is smaller than the prescribed value (1.26 V) so that it is not possible to perform the measurement with a 10-bit precision. Therefore the MCU 31 may output error since the measurement cannot be performed and may cause the display LEDs 44 to indicate the error.

The operation of the lubricant deterioration sensor 10 configured as described above will be now described. The lubricant deterioration sensor 10 is attached to a machine that uses lubricant and is coupled to a power supply. The lubricant deterioration sensor 10 may determine a deterioration degree of the lubricant at regular time intervals. Alternatively the determination of a deterioration degree of the lubricant may be performed whenever need arises or only when a user instructs.

The MCU 31 of the lubricant deterioration sensor 10 may firstly perform the calibration process on the initial detection value of the lubricant and make the detection accuracy maximum within the measurement range. At this point, the MUC 31 may calibrate the detection value in accordance with the detection result from the photodiode 29. For instance, the MCU 31 estimates a deterioration degree of the LED 21 from the detection value output by the photodiode 29 and calibrates the above-mentioned measurement range in light of the estimated deterioration degree. The MUC 31 may also calibrate the intensity of light based on the detection result from the photodiode 29. For instance, the MCU 31 estimates an increase or decrease in the intensity of light emitted from the LED 21 based on the detection value output by the photodiode 29 and calibrates the intensity of light emitted from the LED 21. The MCU 31 may subsequently calculate a brightness and a maximum color-component difference and the like from the calibrated detection value, and compare them with the oil deterioration threshold value and the machine damage threshold value to determine deterioration of the lubricant and damage of the machine respectively. The MCU 31 may show the determination result through the display LEDs 44.

In the above-described embodiment, the lubricant deterioration sensor 10 performs the detection and determination, and then outputs the result. Therefore it is possible to determine a deterioration degree of lubricant with the lubricant deterioration sensor alone without using an external device. Moreover the lubricant deterioration sensor 10 adjusts the measurement range of detection values without using an external device.

According to the above-described embodiment, the following advantageous effects can be obtained. (1) A detection light beam emitted from the LED 21 penetrates lubricant disposed in the oil entering gap 25 and the color sensor 22 detects color information of the detection light that traveled through the lubricant. More specifically, the color sensor 22 obtains a detection value that represents the color information. Subsequently calibration of a measurement range of the detection value detected by the color sensor 22 may be performed by the MCU 31, the digital potentiometer 27, and the operational amplifier 26 in accordance with the lubricant on which the detection is performed. The MCU 31, the digital potentiometer 27, and the operational amplifier 26 serve as a calibration unit. In this way, it is possible to enhance the detection accuracy and the MCU 31 determines a deterioration degree of the lubricant based on the calibrated detection value. Therefore, it is possible to determine a deterioration degree of lubricant with the lubricant deterioration sensor 10 alone without using an external device and to adjust the measurement range of the detection value without using an external device.

(2) The photodiode 29 that directly detects detection light of the LED 21 is provided and the MCU 31 calibrates the intensity of light emitted from the LED 21 in accordance with the detection result from the photodiode 29. When the LED 21 is degraded over time or the intensity of light emitted from the LED 21 is decreased due to temperature change, there may be error caused in the deterioration determination due to change in the detection light caused by the degradation of the LED 21 and the temperature change. However the detection light emitted from the LED 21 can be directly detected so as to check the degradation and temperature change of the LED 21. By calibrating the intensity of light emitted from the LED 21, the determination of a deterioration degree of lubricant will not be affected.

(3) The photodiode 29 that directly detects detection light of the LED 21 is provided and the MCU 31 calibrates a detection value in accordance with the detection result from the photodiode 29. When the LED 21 is degraded over time or the intensity of light emitted from the LED 21 is decreased due to temperature change, there may be error caused in the deterioration determination due to change in the detection light caused by the degradation of the LED 21 and the temperature change. However the detection light emitted from the LED 21 can be directly detected so as to check the degradation and temperature change of the LED 21. By calibrating the detection value, the determination of a deterioration degree of lubricant will not be affected.

(4) The determination unit obtains a plurality of detection values and a mode of the detection values is used for the deterioration determination. In this manner, detection values that largely deviate from the inherent detection value are excluded as noise and detection values that are considered to be correct are used for the determination of lubricant deterioration. Therefore it is possible to enhance the detection accuracy.

(5) The determination unit obtains a plurality of the detection values and a minimum value among the detection values is used for the deterioration determination. In this manner, detection values that are larger than the inherent detection value are excluded as noise and detection values that are considered to be correct are used for the determination of lubricant deterioration. Therefore it is possible to enhance the detection accuracy.

(6) The determination unit uses at least one of a brightness or a maximum color-component difference (a maximum color difference) calculated from the detection value to determine a deterioration degree of lubricant. When lubricant is contaminated with impurities generated from a machine that uses the lubricant, the brightness of the lubricant prominently changes so that a deterioration degree of the lubricant can be easily determined. Moreover, in a case of lubricant in which a color of a base oil is easily changed by oxidation, degradation or the like, the maximum color difference significantly changes so that a deterioration degree of the lubricant can be easily determined. Furthermore, by combining the brightness and the maximum color difference, it is possible to determine a degradation degree of lubricant even when at least one of the contamination or the color change of the base oil occurs in the lubricant.

(7) When there is a prescribed amount of change in the calculated value from the initial value or the calculated value is smaller than the oil deterioration threshold value, the MCU 31 performs determination of a deterioration degree of the lubricant. The initial value of the calculated value is calibrated by the MCU 31, the digital potentiometer 27, and the operational amplifier 26. Because there is a certain amount of change from the initial value, it is possible to easily determine a deterioration degree of the lubricant.

(8) When a machine in which lubricant is used is broken, impurities are generated. The MCU 31 utilizes detection values to determine failure of the machine in which the lubricant is used. In this way, it is possible to easily determine the failure of the machine through the detection value that has changed due to the impurities.

The above-described embodiments can be adequately modified as described below. Failure of a machine is determined from deterioration of lubricant used therein in the above embodiment but only the deterioration of the lubricant may be determined as needed.

In the above embodiment, when there is a certain amount of change in a detection value from the initial value of the detection value, the determination of a deterioration degree of the lubricant is performed. Alternatively, a different prescribed amount of change may be set for a different type of lubricant to perform the determination of a deterioration degree of the lubricant.

A deterioration degree of lubricant is determined based on the brightness and the maximum color-component difference in the above embodiment. Alternatively a deterioration degree of lubricant may be determined based on other calculated values than the brightness and the maximum color-component difference.

In the above embodiment, the minimum value among the obtained detection values is used for the determination. Alternatively if effect of air bubbles or the like to the lubricant is very small, the minimum value may be not necessarily used for the determination.

In the above embodiment, a value that appears most often among the obtained detection values or a mode of the obtained detection values is used for the determination. Alternatively if effect of air bubbles or the like to the lubricant is very small, the mode of the detection values may be not necessarily used for the determination.

In the above embodiment, a mode of the obtained detection values is used for the determination. Alternatively, a median or average of the obtained detection values may be used instead of the mode if noise can be removed.

In the above embodiment, the photodiode 29 is used as the light receiving element that directly detects detection light from the LED 21. Alternatively a phototransistor may be used as long as its responsiveness performance is within an acceptable range.

In the above embodiment, the photodiode 29 directly detects detection light of the LED 21 and the MCU 31 calibrates a detection value in accordance with the detection result from the photodiode 29. However the calibration of the detection value may not be performed when an effect of degradation of the LED 21 is very small and within an acceptable range.

In the above embodiment, the photodiode 29 directly detects detection light of the LED 21 and the MCU 31 calibrates the intensity of the light in accordance with the detection result from the photodiode 29. However the calibration of the intensity of light emitted from the LED 21 may not be performed when an effect of degradation of the LED 21 is very small and within an acceptable range.

In the above embodiment, the optical sensor is a reflection type using a prism. However, other types of optical sensors such as one in which the light emitting element is disposed so as to face the light receiving element in the optical sensor unit may also be used. In the above embodiment, the machine may be a machine equipped with a movable bearing, a piston and the like that requires lubricant to move. Moreover, the machine may be wind generators, construction machines, aircrafts, railroad vehicles, vacuum pumps and the like. More specifically, the wind generator may include, for example, a step-up gear and its bearing for the wind generator, a pitch-driving hydraulic cylinder and a reduction gear, and a YAW driving hydraulic motor. As for the construction machine, it may include, for example, a hydraulic motor, a hydraulic cylinder, a hydraulic valve (a load sensing valve and the like), a drive motor, a rotary motor, a joint and the like. As for the aircraft, it may include, for example, a flight control actuator, a hydraulic motor and the like that drives a spoiler, an aileron, an elevator, an ladder, a flap, a slat, a brake, a steering and the like. As for the railroad vehicle, it may include, for example, an air compressor for the railroad vehicles. As for a commercial vehicle and a passenger vehicle, they may include, for example, a break actuator, a circulation pump for an engine oil, a supply pump for fuel and the like. As for a vessel, it may include, a for example, a circulation pump for an engine oil, a supply pump for fuel, a hydraulically-actuated device and equipment, and the like.

LIST OF REFERENCE NUMBERS 10 lubricant deterioration sensor
11 housing
11a container section
11b bottom
11c first through hole
11d second through hole
12 circuit substrate
20 optical sensor unit
21 LED as light emitting element
22 color sensor as light receiving element
23 first prism
23a incident surface
23b reflection surface
23c exit surface
24 second prism
24a incident surface
24b reflection surface
24c exit surface
25 oil entering gap serving as examination section
26 operational amplifier serving as calibration unit
27 digital potentiometer serving as calibration unit
28 LED driver
29 photodiode
30 control unit
31 MCU serving as calibration unit and determination unit
32 A/D converter circuit
33 D/A converter circuit
34 EEPROM
40 external interface unit
41 power supply
42 USB
43 contact point
44 display LEDs

What is claimed is:

1. A lubricant deterioration sensor, comprising:
   an examination section in which lubricant to be detected enters;
   a light emitting element emitting detection light to the examination section;
   a light receiving element obtaining a detection value that represents color information of the detection light traveled through the lubricant;
   a calibration unit calibrating a measurement range of the detection value in accordance with the lubricant to be detected;
   a determination unit configured to:
      obtain a plurality of the detection values, the plurality of the detection values comprising detection values for portions of the lubricant containing air bubbles and a detection value for a portion of the lubricant that does not contain air bubbles,
      determine color information of the detection light traveled through the portion of the lubricant that does not contain air bubbles based on a mode of the plurality of the detection values, the mode of the detection values differentiating the detection values for the portions of the lubricant containing air bubbles from the detection value for the portion of the lubricant that does not contain air bubbles, and
      determine a deterioration degree of the lubricant based on the determined color information; and
   a housing in which the examination section, the light emitting element, the light receiving element, the calibration unit, and the determination unit are disposed.

2. The lubricant deterioration sensor of claim 1, wherein the light receiving element is a first light receiving element, wherein the lubricant deterioration sensor further includes a second light receiving element that detects detection light emitted from the light emitting element and obtains a detection result, and wherein the calibration unit calibrates an intensity of light emitted from the light emitting element in accordance with the detection result.

3. The lubricant deterioration sensor of claim 1, wherein the light receiving element is a first light receiving element, wherein the lubricant deterioration sensor further includes a second light receiving element that detects detection light emitted from the light emitting element and obtains a detection result, and wherein the calibration unit calibrate the detection result in accordance with the detection result.

4. The lubricant deterioration sensor of claim 1, wherein the determination unit is configured to determine the deterioration degree of the lubricant based on a calculated value using at least one of a brightness or a maximum color-component difference calculated from the detection value.

5. The lubricant deterioration sensor of claim 4, wherein the calibration unit obtains an initial value by calibrating the calculated value, and wherein the determination unit is configured to perform determination of the deterioration degree of the lubricant when there is a prescribed amount of change in the calculated value from the initial value.

6. The lubricant deterioration sensor of claim 1, wherein the determination unit is configured to determine damage of a machine that uses the lubricant based on the detection value.

7. A lubricant deterioration sensor, comprising:
an examination section in which lubricant to be detected enters;
a light emitting element emitting detection light to the examination section;
a light receiving element obtaining a detection value that represents color information of the detection light traveled through the lubricant;
a calibration unit calibrating a measurement range of the detection value in accordance with the lubricant to be detected;
a determination unit configured to:
  determine whether the lubricant is colored based on the detection value, and, if the lubricant is colored,
    obtain a plurality of the detection values, the plurality of the detection values comprising detection values for portions of the lubricant containing air bubbles and a detection value for a portion of the lubricant that does not contain air bubbles,
    determine color information of the detection light traveled through the portion of the lubricant that does not contain air bubbles based on a minimum value among the plurality of the detection values, the minimum value of the detection values differentiating the detection values for the portions of the lubricant containing air bubbles from the detection value for the portion of the lubricant that does not contain air bubbles, and
    determine a deterioration degree of the lubricant based on the determined color information; and
a housing in which the examination section, the light emitting element, the light receiving element, the calibration unit, and the determination unit are disposed.

8. A lubricant deterioration sensor, comprising:
an examination section in which lubricant to be detected enters;
a light emitting element emitting detection light to the examination section;
a light receiving element obtaining a detection value that represents color information of the detection light traveled through the lubricant;
a calibration unit calibrating a measurement range of the detection value in accordance with the lubricant to be detected;
a determination unit configured to:
  determine whether the lubricant is colored based on the detection value, and, if the lubricant is not colored,
    obtain a plurality of the detection values, the plurality of the detection values comprising detection values for portions of the lubricant containing air bubbles and a detection value for a portion of the lubricant that does not contain air bubbles,
    determine color information of the detection light traveled through the portion of the lubricant that does not contain air bubbles based on a maximum value among the plurality of the detection values, the maximum value of the detection values differentiating the detection values for the portions of the lubricant containing air bubbles from the detection value for the portion of the lubricant that does not contain air bubbles, and
    determine a deterioration degree of the lubricant based on the determined color information; and
a housing in which the examination section, the light emitting element, the light receiving element, the calibration unit, and the determination unit are disposed.

* * * * *